US009662040B2

(12) United States Patent
Kam et al.

(10) Patent No.: US 9,662,040 B2
(45) Date of Patent: May 30, 2017

(54) COMPUTER-AIDED DIAGNOSIS APPARATUS AND METHOD

(71) Applicant: Samsung Electronics Co., Ltd., Suwon-si (KR)

(72) Inventors: Hye Jin Kam, Seongnam-si (KR); Ha Young Kim, Yongin-si (KR); Joo Hyuk Jeon, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 93 days.

(21) Appl. No.: 14/825,638

(22) Filed: Aug. 13, 2015

(65) Prior Publication Data

US 2016/0048972 A1     Feb. 18, 2016

(30) Foreign Application Priority Data

Aug. 14, 2014 (KR) .................. 10-2014-0106268

(51) Int. Cl.
| | | |
|---|---|---|
| G06T 7/00 | (2006.01) | |
| A61B 5/055 | (2006.01) | |
| G06T 7/174 | (2017.01) | |
| A61B 8/08 | (2006.01) | |
| A61B 8/00 | (2006.01) | |
| A61B 6/03 | (2006.01) | |

(Continued)

(52) U.S. Cl.
CPC ............ *A61B 5/055* (2013.01); *G06T 7/0016* (2013.01); *G06T 7/174* (2017.01); *A61B 6/032* (2013.01); *A61B 6/12* (2013.01); *A61B 6/469* (2013.01); *A61B 6/5217* (2013.01); *A61B 8/085* (2013.01); *A61B 8/469* (2013.01); *A61B 8/5223* (2013.01); *G06T 2207/10016* (2013.01); *G06T 2207/10132* (2013.01); *G06T 2207/30096* (2013.01)

(58) Field of Classification Search
CPC ....... G06T 7/0012; G06T 7/0016; G06T 7/11; G06T 7/174; G06T 2207/20112; G06T 2207/20168; A61B 6/469; A61B 6/5217; A61B 8/469; A61B 8/5223
See application file for complete search history.

(56) References Cited

U.S. PATENT DOCUMENTS

| 7,088,850 B2 | 8/2006 | Wei et al. |
| 7,615,008 B2 | 11/2009 | Zhang et al. |

(Continued)

FOREIGN PATENT DOCUMENTS

JP        5274834 B2      5/2013

OTHER PUBLICATIONS

H. Mobahi, et al., "Deep Learning from Temporal Coherence in Video," Proceedings of the 26th International Conference on Machine Learning, Jun. 14-18, 2009, at Montreal, Canada (8 pages, in English).

(Continued)

*Primary Examiner* — Andrew W Johns
(74) *Attorney, Agent, or Firm* — Jefferson IP Law, LLP

(57) ABSTRACT

A computer-aided diagnosis (CAD) apparatus and method. The CAD apparatus includes an area divider configured to divide a current image frame into a first area and a second area based on location of a region of interest (ROI) detected in a previous image frame. The CAD apparatus further includes a functional processor configured to perform different functions of the CAD apparatus for the first area and the second area.

19 Claims, 7 Drawing Sheets

(51) Int. Cl.
  *A61B 6/12* (2006.01)
  *A61B 6/00* (2006.01)

(56) References Cited

U.S. PATENT DOCUMENTS

| 7,992,100 B2 | 8/2011 | Lundstrom et al. |
| 2006/0251301 A1 | 11/2006 | McNamara, Jr. et al. |
| 2007/0183661 A1* | 8/2007 | El-Maleh et al. ............ 382/173 |

OTHER PUBLICATIONS

T. Liu, et al., "Learning to Detect a Salient Object," IEEE Transactions on Pattern Analysis and Machine Intelligence, vol. 33, No. 2, Dec. 2009, pp. 1-15.

* cited by examiner

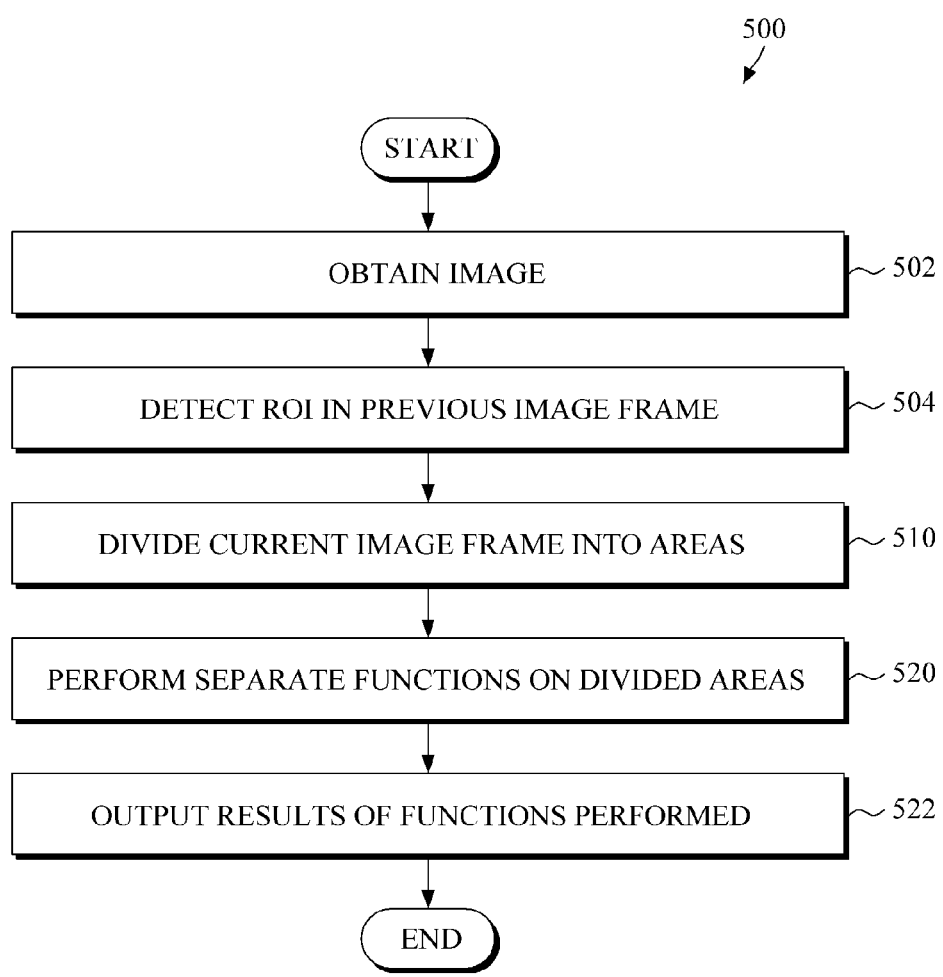

COMPUTER-AIDED DIAGNOSIS APPARATUS AND METHOD

CROSS-REFERENCE TO RELATED APPLICATION(S)

This application claims the benefit under 35 U.S.C. §119 (a) of Korean Patent Application No. 10-2014-0106268, filed on Aug. 14, 2014, in the Korean Intellectual Property Office, the entire disclosure of which is incorporated herein by reference for all purposes.

BACKGROUND

1. Field

The following description relates to a computer-aided diagnosis apparatus and method.

2. Description of Related Art

A computer-aided diagnosis (CAD) system refers to a system that analyzes medical images, such as ultrasound images, and displays suspicious areas from the medical images based on analysis results, thereby assisting doctors in a diagnostic procedure. Diagnosis is a difficult process because of the uncertainty that is caused by human limitations in recognizing an illness. As such, utilizing a CAD system may prove to be advantageous because it not only reduces the probability of the aforementioned dilemma, but also lessens the doctor's workload with regard to reading individual diagnostic images.

However, a drawback of a CAD system is that it detects a region of interest (ROI) in each image frame and tracks or classifies the detected ROI in each image frame, thus making the CAD system difficult to operate in real time.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, a computer-aided diagnosis (CAD) apparatus includes: an area divider configured to divide a current image frame into a first area and a second area based on location of a region of interest (ROI) detected in a previous image frame; and a functional processor configured to perform different functions of the CAD apparatus for the first area and the second area.

The first area may include an area that extends radially from a same point as a center point of the ROI in the previous image frame and the second area may be an outlying area in the current image frame.

A radial extension of the first area may be determined based on at least one of the following previously collected lesion data factors: a distribution of a specific lesion in the current image frame, the specific lesion being similar to a lesion within the ROI in the previous image frame, a length of the specific lesion, changes in an area of the specific lesion, and a degree of change in shape of the specific lesion.

The functional processor may be configured to include a first functional configured to perform on the first area at least one of following functions: an ROI check, lesion segmentation, and lesion classification, and a second functional module configured to perform ROI detection on the second area.

The first functional module may be configured to, for the ROI check, extract feature values from the first area, and determine whether the first area corresponds to the ROI based on similarities between the extracted feature values and feature values of the ROI in the previous image frame.

The first functional module may be configured to, for the lesion classification, extract feature values from the first area and determine whether a lesion in the first area is malignant or benign by comparing a previously stored diagnostic model to the extracted feature values.

The CAD apparatus may further include an ROI detector configured to detect the ROI in the previous image frame.

The CAD apparatus may further include a screen display configured to output to a screen the current image frame and results functions performed by the functional processor.

In another general aspect, there is provided a computer-aided diagnosis (CAD) method including: dividing, using an area divider, a current image frame into a first area and a second area based on location of a region of interest (ROI) detected in a previous image frame; and performing, using a functional processor, different functions of the CAD apparatus for the first area and the second area.

The first area may include an area that extends radially from a same point as a center point of the ROI in the previous image frame and the second area may be an outlying area in the current image frame.

A radial extension of the first area may be determined based on at least one of the following previously collected lesion data factors: a distribution of a specific lesion in the current image frame, the specific lesion being similar to a lesion within the ROI in the previous image frame, a length of the specific lesion, changes in an area of the specific lesion, and a degree of change in shape of the specific lesion.

The performing of the different functions may include performing at least one of an ROI check, lesion segmentation, and lesion classification in the first area A, while performing ROI detection in the second area.

The performing of the ROI check may include extracting feature values from the first area and determining whether the first area corresponds to the ROI based on similarities between the extracted feature values and feature values of the ROI in the previous image frame.

The performing of the lesion classification may include extracting feature values from the first area and determining whether a lesion in the first area is malignant or benign by comparing the extracted feature values to a previously stored diagnostic model.

The CAD method may further include detecting the ROI in the previous image frame.

The CAD method may further include outputting to a screen the current image frame and results of functions that are performed by the functional module.

In yet another general aspect, a computer-aided diagnosis (CAD) apparatus may include an area divider configured to determine a first area of a current image frame, wherein the first area comprises an area that extends radially from a same point as a center point of a region of interest (ROI) detected in a previous image frame, and wherein the first area has a radial extension determined based on previously collected lesion data factors. The CAD apparatus may include a functional processor configured perform at least one of an ROI check, lesion segmentation, and lesion classification on the first area.

The area divider may be configured to determine a second area of the current image frame which is an outlying area in the current image frame, the functional processor may be configured to perform ROI detection on the second area.

The first area and the second area may each comprise an overlap area that is a region in which the first area and the second area overlap each other.

Other features and aspects will be apparent from the following detailed description, the drawings, and the claims.

BRIEF DESCRIPTION OF THE DRAWINGS

FIG. 5 is a flowchart illustrating an example of a CAD method.

Throughout the drawings and the detailed description, the same reference numerals refer to the same elements. The drawings may not be to scale, and the relative size, proportions, and depiction of elements in the drawings may be exaggerated for clarity, illustration, and convenience.

DETAILED DESCRIPTION

The following description is provided to assist the reader in gaining a comprehensive understanding of the methods, apparatuses, and/or systems described herein. However, various changes, modifications, and equivalents of the methods, apparatuses, and/or systems described herein will be apparent to those of ordinary skill in the art. The sequences of operations described herein are merely examples, and are not limited to those set forth herein, but may be changed as will be apparent to one of ordinary skill in the art, with the exception of operations necessarily occurring in a certain order. Also, descriptions of well-known functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

Figure 1:
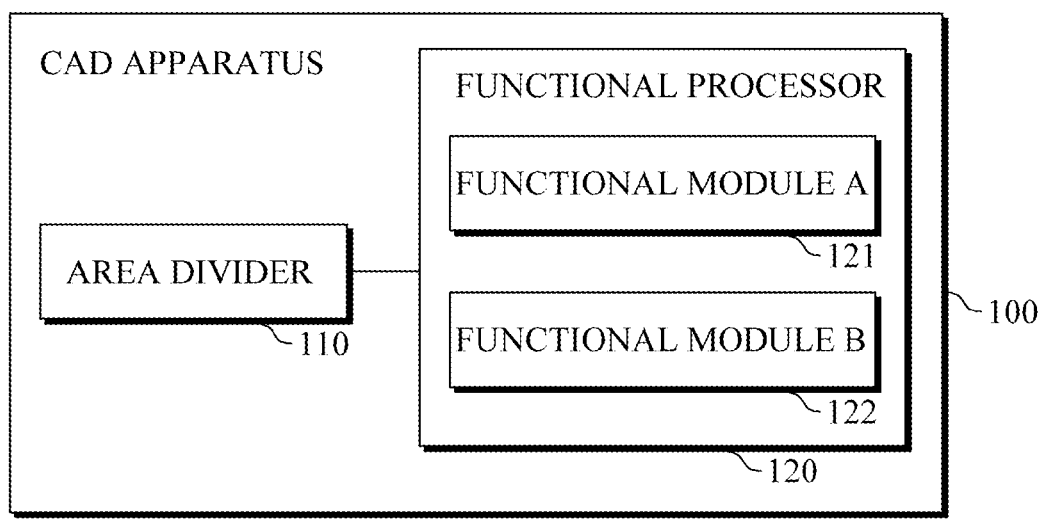
FIG. 1 is a diagram illustrating an example of a computer-aided diagnosis (CAD) apparatus.

FIG. 1 is a diagram illustrating an example of a computer-aided diagnosis (CAD) apparatus, according to an embodiment.

Referring to FIG. 1, the CAD apparatus 100 may include an area divider 110 and a functional processor 120.

The area divider 110 may divide a current image frame into first and second areas, which are respectively referred to as 'area A' and 'area B', based on the location of a region of interest (ROI) that was detected in a previous image frame. Here, an ROI may include, for example, a lesion of unspecified nature, an area with unusual features, or a malignant lesion.

In this example, the area divider 110 may divide the current image frame into area A and area B, wherein the area A includes an area that extends radially from the same point as the center point of the ROI in the previous image frame and the area B is the remaining area of the current image frame.

At this time, parameters for radial extension may be obtained from a variety of existing medical databases. For example, such parameters may be determined based on lesion data collected in the existing medical databases including information relevant to the lesion within the ROI of the previous image frame (e.g., distribution of a lesion, length of a lesion, changes in a lesion area, degree of change in lesion shape, and the like).

In addition, depending on the accuracy, sensitivity, or the like of the apparatus 100, area A and area B may both include a portion that is an overlap of said two areas. In other words, if needed, area A and area B may each include an overlap, which is a boundary region that is limited to a certain range according to a predefined set of values.

The functional processor 120 may perform different functions of the apparatus 100 for area A and area B. To this end, the functional module 120 may include two functional modules: functional module A 121 and functional module B 122.

The functional module A 121 may perform a function (hereinafter, referred to as an "ROI check") to determine whether or not the area A corresponds to the ROI of the previous image frame. That is, the functional processor A 121 may perform the ROI check to determine whether or not the area A is the ROI. More specifically, functional module A 121 may extract feature values by analyzing area A, and identifying the similarity between the feature values of area A and feature values of the ROI in the previous image frame. If the similarity is equal to or greater than a predefined threshold, area A is determined as corresponding to the ROI.

Here, features of an ROI refer to characteristics that help determine whether an ROI in an image is a lesion or not, and the feature values refer to values that quantify the features. For example, the features may include the shape, margin, echo pattern, orientation, boundary, and textual features of a lesion within an ROI.

Functional module A 121 segments the lesion in area A. More specifically, functional module A 121 may precisely segment a lesion in area A using various lesion segmentation methods. The lesion segmentation methods may include thresholding, clustering, region growing, splitting and merging, graph partitioning, edge detection, as well as methods which are compression-based, histogram-based, and the like.

Functional module A 121 performs lesion classification on area A. More specifically, functional module A 121 may extract feature values by analyzing area A, and determine whether the lesion in area A is malignant or benign by comparing the extracted feature values to a previously built diagnostic model.

Here, the diagnostic model may be formed based on learned medical data of diagnosed patients, whereby this diagnostic model may be stored in an internal or external database of the apparatus 100. The learning algorithm used for building the diagnostic model may be a deep-learning-based algorithm that may include convolutional neural network (CNN), recurrent neural network (RNN), sparse auto-encoder, deformable part model (DPM), support vector machine (SVM), histogram of oriented gradients (HOG), and the like.

When performing lesion classification on area A, functional module A 121 may use feature values extracted from the ROI in the previous image frames, as well as the feature values extracted from area A of the current image frame.

Functional module A 121 may perform one of the following functions, or may perform two or more of the following functions simultaneously or sequentially: ROI check, lesion segmentation, and lesion classification.

Functional module B 122 may detect for ROI in area B. For example, functional module B 122 may extract feature values from area B using various existing filters, such as a radial gradient index (RGI), average radial gradient (ARD), hybrid filtering, and multi-fractal analysis; simple grayscale thresholding; or a deep-learning-based algorithm, such as CNN, RNN, sparse auto-encoder, DPM, SVM, and HOG. Functional module B may then detect the ROI based on the extracted feature values.

Figure 2:
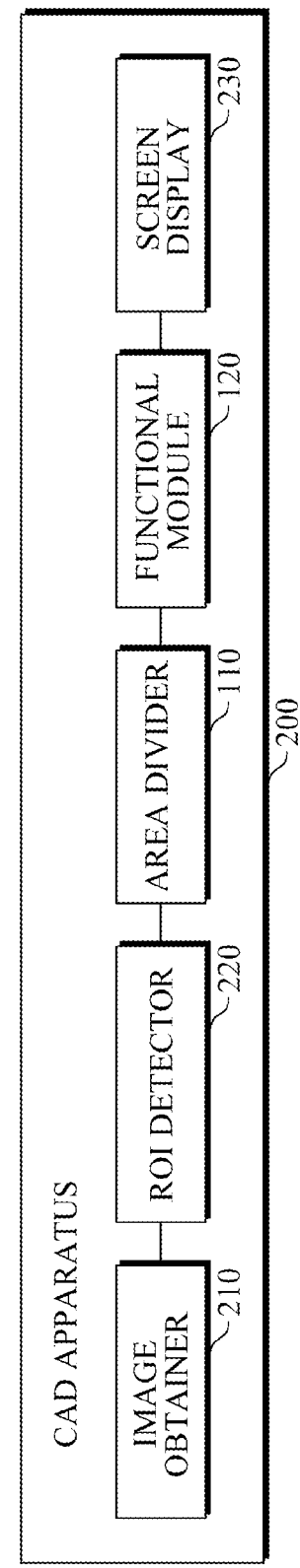
FIG. 2 is a diagram illustrating another example of a CAD apparatus.

FIG. 2 is a diagram illustrating another example of a CAD apparatus.

Referring to FIG. 2, the CAD apparatus 200 may optionally include an image obtainer 210, an ROI detector 220, and a screen display 230, in addition to elements of the CAD apparatus 100 shown in FIG. 1.

The image obtainer 210 obtains medical images of a patient. Here, the medical images may be real-time ultrasound images in frames obtained through a probe. In addition, the medical images may be a set of three-dimensional (3D) image slices obtained from a computed tomography (CT) device or a magnetic resonance imaging (MRI) device. In this case, each of the image slices would correspond to each image frame.

The ROI detector 220 detects the ROI by analyzing image frames previously obtained by the image obtainer 210. For example, the ROI detector 220 may extract feature values from the previously obtained image frames using various existing filters, such as a radial gradient index (RGI), average radial gradient (ARD), hybrid filtering, and multi-fractal analysis. Alternatively, the ROI detector 220 may extract the feature values using simple grayscale thresholding or a deep-learning-based algorithm, such as CNN, RNN, sparse auto-encoder, DPM, SVM, and HOG. The ROI detector may then detect the ROI based on the extracted feature values.

The screen display 230 may output to a screen the current image frame together with results of performing the functions by the functional module 120. That is, the screen display 230 may output to the screen the current image frame obtained in real time and the function performing results, i.e., a result of an ROI check, a result of lesion segmentation, and a result of ROI detection.

In addition, the screen display 230 may place a box around the detected ROI and mark the location of the detected ROI with a cross at the center of the ROI. However, the aspects of the present disclosure are not limited thereto. For example, the screen display 230 may indicate the ROI using a mark of various shapes, such as a circle, a triangle, or the like, and the ROI may be indicated using a color code in which a variety of colors may be used.

Moreover, the screen display 230 may display on a single screen or on multiple screens the results of the functions carried out by the functional module 120.

Figure 3:
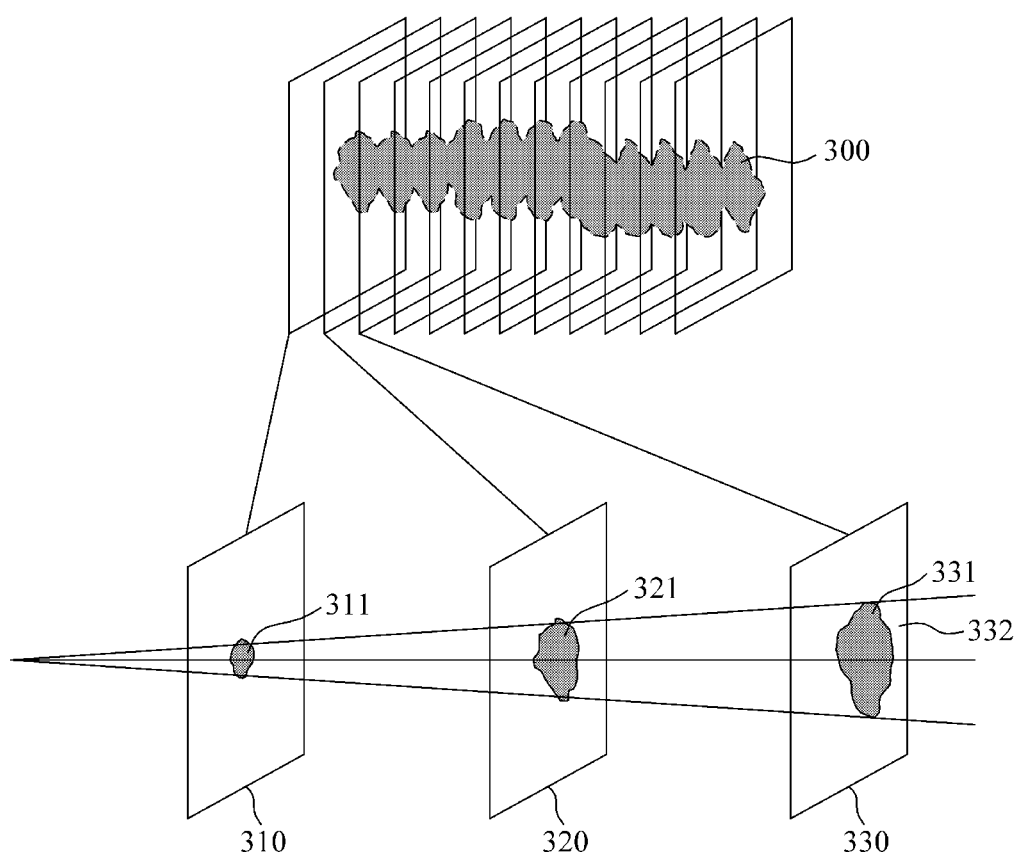
FIG. 3 is a diagram for explaining a principle of a CAD apparatus.

FIG. 3 is a diagram explaining a principle of a CAD apparatus.

Due to a recognizable size, it is assumed that a lesion that is to be examined is sizable enough so that it is possible to observe it in successive image frames. In other words, rather than being a lesion that is observable in only a single frame, the lesion can be continuously observed in two or more consecutive image frames.

If a suspected area is detected in two or more consecutive image frames, it is highly likely that a lesion with the same center point as that of the suspected area detected in the previous image frames will be observed in the following image frame, whereby the suspected area may change in its shape and size.

As shown in FIG. 3, a lesion 300 is observed continuously in a number of consecutive image frames. Accordingly, the CAD apparatus 100 and 200 may divide a current image frame 330 into area A 331 and area B 332, wherein the area A 331 is connected to ROIs 311 and 321 in the previous image frames 310 and 320, while area B 332 is the outlying area in the current image frame 330; the CAD apparatus 100 and 200 may then perform separate functions on area A 331 and area B 332 (e.g., lesion classification on area A 331 and new ROI detection on area B 332), so that the accuracy and speed of lesion detection/classification can be enhanced.

Figure 4A:
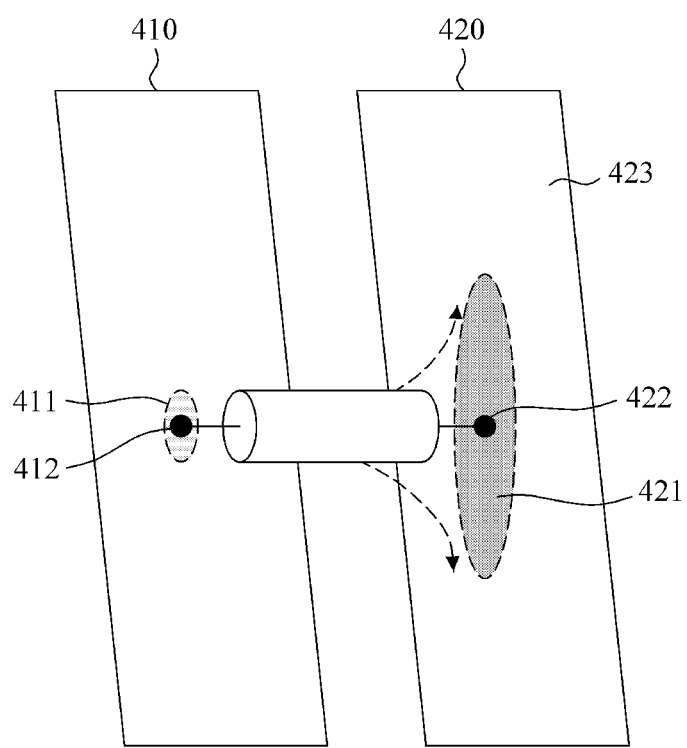
FIG. 4A is a diagram illustrating a method of dividing a current image frame into a two areas, referred to as 'area A' and 'area B'.
Figure 4B:
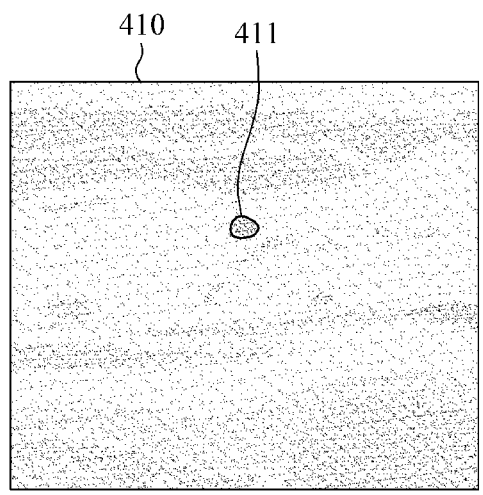
FIG. 4B is a diagram illustrating an example of a previous image frame.
Figure 4C:
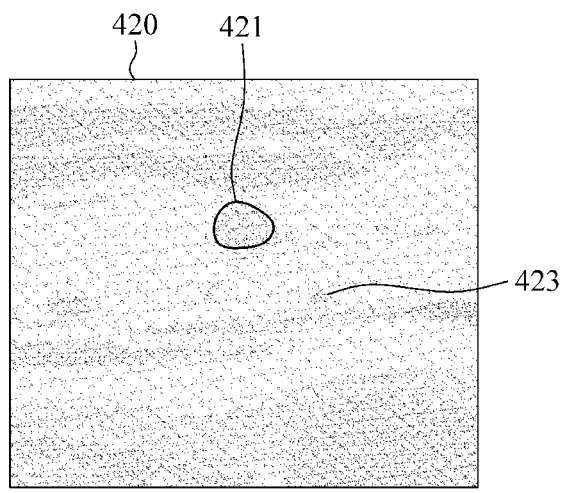
FIG. 4C is a diagram illustrating an example of a current image frame in which areas are divided.

FIGS. 4A to 4C are diagrams explaining procedures for dividing a current image frame into area A and area B. Specifically, FIG. 4A is a diagram illustrating a method of dividing a current image frame into area A and area B, FIG. 4B is a diagram illustrating an example of a previous image frame, and FIG. 4C is a diagram illustrating an example of the current image frame in which the areas A and B are divided.

Referring to FIG. 4A, an area divider 110 divides a current image frame 410 into area A 421 and area B 423 based on the location of an ROI 411 detected in a previous image frame 410. More specifically, the area divider 110 divides a certain area of the current image frame 420 by taking the center point 412 of the ROI 411 of the previous image frame 410 and drawing an enclosed area based on a predetermined radius. The area that lies within the enclosure and has a center point 422 is area A 421, while the outlying area is area B 423.

In this case, the area that lies within the enclosure in the current image frame 420 may be formed in an irregular or rectangular shape extending from the same point 422 as the center point 412 of the ROI 411 in the previous image frame 410. The shape of the enclosed area depicted in the present disclosure is provided only as an example, and the area may be extended in various forms according to the performance or use of the system.

As described above, parameters for radial extension may be obtained from a variety of existing medical databases. For example, such parameters may be determined based on lesion data collected from existing medical databases and which may include information regarding a lesion that is similar to the lesion within the ROI of the previous image frame. Information that is of interest regarding a similar lesion may include the distribution of a lesion, length of a lesion, changes in a lesion area, degree of change in lesion shape, and the like.

Referring to FIGS. 4A to 4C, when the ROI 411 was detected in a previous image frame 410, the current image frame 420 may be divided into area A 421 and area B 423 based on the location of the ROI 411 in the previous image frame 410.

FIG. 5 is a flowchart illustrating an example of a CAD method, according to an embodiment.

Referring to FIG. 5, the CAD method 500 may include an operation 502 in which medical images of a patient are obtained. Here, the medical images may be real-time ultrasound images obtained through a probe in units of frames. Further, the medical images may be a set of 3D image slices obtained through a CT device, an MRI device, or the like. In this case, each of the image slices may correspond to each image frame.

The CAD method 500 may further include operation 504 in which an ROI is detected by analyzing previous image frames obtained in operation 502. For example, the CAD apparatus 200 may extract feature values from the previous image frame using various existing filters, such as a radial gradient index (RGI), average radial gradient (ARD), hybrid filtering, and multi-fractal analysis. Alternatively, the CAD apparatus 200 may extract feature values from the previous image frame using simple grayscale thresholding or a deep-learning-based algorithm, such as CNN, RNN, sparse auto-encoder, DPM, SVM, and HOG. The CAD apparatus 200 may then detect the ROI based on the extracted feature values.

In operation 510 of the CAD method, a current image frame is divided into area A and area B based on the location of an ROI detected in a previous image frame. For example, the CAD apparatus 100 and 200 (refer to FIG. 1 and FIG. 2) may divide the current image frame into the area A and the area B, wherein area A includes an enclosed area that has the same center point as the center point of the ROI in the previous image frame, and area B is the outlying area in the current image frame.

At this time, as described above, parameters for radial extension may be obtained from a variety of existing medical databases. Areas A and B may each include a boundary region therebetween according to accuracy, sensitivity, or the like of the apparatus 100 or 200.

Thereafter, in operation 520, the CAD apparatus carries out separate functions in area A and area B. For example, the CAD apparatus 100 and 200 may perform an ROI check, lesion segmentation, and lesion classification on area A, while performing ROI detection on area B.

In this case, the ROI check, lesion segmentation, and lesion classification for area A and the ROI detection for area B are described in detail above with reference to FIG. 1, and thus the detailed descriptions thereof will be omitted here.

The CAD method 500 may further include operation 522 in which the current image frame and the function performance results are both output to a screen.

For example, the CAD apparatus 200 may output to the screen the current image frame that is obtained in real time. The CAD apparatus 200 may also output to the screen the results of having performed various functions such as an ROI check result, a lesion segmentation result, a lesion classification result, and/or a lesion detection result.

The apparatuses, units, modules, devices, and other components illustrated in FIGS. 1 and 2 that perform the operations described herein with respect to FIGS. 3-5 are implemented by hardware components. Examples of hardware components include controllers, sensors, generators, drivers, and any other electronic components known to one of ordinary skill in the art. In one example, the hardware components are implemented by one or more processors or computers. A processor or computer is implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices known to one of ordinary skill in the art that is capable of responding to and executing instructions in a defined manner to achieve a desired result. In one example, a processor or computer includes, or is connected to, one or more memories storing instructions or software that are executed by the processor or computer. Hardware components implemented by a processor or computer execute instructions or software, such as an operating system (OS) and one or more software applications that run on the OS, to perform the operations described herein with respect to FIGS. 3-5. The hardware components also access, manipulate, process, create, and store data in response to execution of the instructions or software. For simplicity, the singular term "processor" or "computer" may be used in the description of the examples described herein, but in other examples multiple processors or computers are used, or a processor or computer includes multiple processing elements, or multiple types of processing elements, or both. In one example, a hardware component includes multiple processors, and in another example, a hardware component includes a processor and a controller. A hardware component has any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods illustrated in FIGS. 3-5 that perform the operations described herein with respect to FIGS. 1 and 2 are performed by a processor or a computer as described above executing instructions or software to perform the operations described herein.

Instructions or software to control a processor or computer to implement the hardware components and perform the methods as described above are written as computer programs, code segments, instructions or any combination thereof, for individually or collectively instructing or configuring the processor or computer to operate as a machine or special-purpose computer to perform the operations performed by the hardware components and the methods as described above. In one example, the instructions or software include machine code that is directly executed by the processor or computer, such as machine code produced by a compiler. In another example, the instructions or software include higher-level code that is executed by the processor or computer using an interpreter. Programmers of ordinary skill in the art can readily write the instructions or software based on the block diagrams and the flow charts illustrated in the drawings and the corresponding descriptions in the specification, which disclose algorithms for performing the operations performed by the hardware components and the methods as described above.

The instructions or software to control a processor or computer to implement the hardware components and perform the methods as described above, and any associated data, data files, and data structures, are recorded, stored, or fixed in or on one or more non-transitory computer-readable storage media. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, and any device known to one of ordinary skill in the art that is capable of storing the instructions or software and any associated data, data files, and data structures in a non-transitory manner and providing the instructions or software and any associated data, data files, and data structures to a processor or computer so that the processor or computer can execute the instructions. In one example, the instructions or software and any associated data, data files, and data structures are distributed over network-coupled computer systems so that the instructions and software and any associated data, data files, and data structures are stored, accessed, and executed in a distributed fashion by the processor or computer.

The screen display described herein may be implemented using a liquid crystal display (LCD), a light-emitting diode (LED) display, a plasma display panel (PDP), a screen, a terminal, or any other type of display known to one of ordinary skill in the art. A screen may be a physical structure that includes one or more hardware components that provide the ability to render a user interface and receive user input. The screen may include any combination of a display region, a gesture capture region, a touch-sensitive display, and a configurable area. The screen may be part of an apparatus, or may be an external peripheral device that is attachable to and detachable from the apparatus. The screen display may be a single-screen display or a multi-screen display. A single physical screen may include multiple displays that are managed as separate logical displays permitting different content to be displayed on separate displays even though they are part of the same physical screen.

The user interface may provide the capability of inputting and outputting information regarding a user and an image. The user interface may include a network module for connecting to a network and a universal serial bus (USB) host module for forming a data transfer channel with a mobile storage medium. In addition, the user interface may include one or more input/output devices, such as a mouse, a keyboard, a touch screen, a monitor, a speaker, a screen, or a software module for controlling the input/output device.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A computer-aided diagnosis (CAD) apparatus comprising:
   at least one processor; and
   at least one memory storing one or more computer programs configured to be executed by the at least one processor, the one or more computer programs including instructions to:
   divide a current image frame into a first area and a second area based on location of a region of interest (ROI) detected in a previous image frame, and
   perform different functions of the CAD apparatus for the first area and the second area.

2. The CAD apparatus of claim 1, wherein the first area includes an area that extends radially from a same point as a center point of the ROI in the previous image frame and the second area is an outlying area in the current image frame.

3. The CAD apparatus of claim 2, wherein a radial extension of the first area is determined based on at least one of the following previously collected lesion data factors: a distribution of a specific lesion in the current image frame, the specific lesion being similar to a lesion within the ROI in the previous image frame, a length of the specific lesion, changes in an area of the specific lesion, and a degree of change in shape of the specific lesion.

4. The CAD apparatus of claim 1, wherein the at least one processor is further configured to:
   perform on the first area at least one of an ROI check, lesion segmentation, and lesion classification, and
   perform ROI detection on the second area.

5. The CAD apparatus of claim 4, wherein the at least one processor is further configured to:
   extract, for the ROI check, feature values from the first area, and determine whether the first area corresponds to the ROI based on similarities between the extracted feature values and feature values of the ROI in the previous image frame.

6. The CAD apparatus of claim 4, wherein the at least one processor is further configured to:
   extract, for the lesion classification, feature values from the first area, and
   determine whether a lesion in the first area is malignant or benign by comparing a previously stored diagnostic model to the extracted feature values.

7. The CAD apparatus of claim 1,
   wherein the at least one processor is further configured to detect the ROI in the previous image frame.

8. The CAD apparatus of claim 1, further comprising:
   a screen configured to display the current image frame and results of functions performed by the at least one processor.

9. A computer-aided diagnosis (CAD) method comprising:
   dividing, using at least one processor, a current image frame into a first area and a second area based on location of a region of interest (ROI) detected in a previous image frame; and
   performing, using the at least one processor, different functions of the CAD apparatus for the first area and the second area.

10. The CAD method of claim 9, wherein the first area includes an area that extends radially from a same point as a center point of the ROI in the previous image frame and the second area is an outlying area in the current image frame.

11. The CAD method of claim 10, wherein a radial extension of the first area is determined based on at least one of the following previously collected lesion data factors: a distribution of a specific lesion in the current image frame, the specific lesion being similar to a lesion within the ROI in the previous image frame, a length of the specific lesion, changes in an area of the specific lesion, and a degree of change in shape of the specific lesion.

12. The CAD method of claim 9, wherein the performing of the different functions comprises performing at least one of an ROI check, lesion segmentation, and lesion classification in the first area, while performing ROI detection in the second area.

13. The CAD method of claim 12, wherein the performing of the ROI check comprises extracting feature values from the first area and determining whether the first area corresponds to the ROI based on similarities between the extracted feature values and feature values of the ROI in the previous image frame.

14. The CAD method of claim 12, wherein the performing of the lesion classification comprises extracting feature values from the first area and determining whether a lesion in the first area is malignant or benign by comparing the extracted feature values to a previously stored diagnostic model.

15. The CAD method of claim 9, further comprising: detecting the ROI in a previous image frame.

16. The CAD method of claim 9, further comprising:
outputting to a screen the current image frame and results of functions that are performed by the at least one processor.

17. A computer-aided diagnosis (CAD) apparatus comprising:
at least one processor; and
at least one memory storing one or more computer programs configured to be executed by the at least one processor, the one or more computer programs including instructions to:
determine a first area of a current image frame, wherein the first area comprises an area that extends radially from a same point as a center point of a region of interest (ROI) detected in a previous image frame, and wherein the first area has a radial extension determined based on previously collected lesion data factors, and
perform at least one of an ROI check, lesion segmentation, and lesion classification on the first area.

18. The CAD apparatus of claim 17, wherein the at least one processor is further configured to:
determine a second area of the current image frame which is an outlying area in the current image frame, and
perform ROI detection on the second area.

19. The CAD apparatus of claim 18, wherein the first area and the second area each comprise an overlap area that is a region in which the first area and the second area overlap each other.

\* \* \* \* \*